United States Patent
Diaz et al.

(10) Patent No.: US 12,414,763 B2
(45) Date of Patent: Sep. 16, 2025

(54) WOUND CLOSURE DEVICE

(71) Applicant: B. Braun Surgical S.A., Rubi (ES)

(72) Inventors: Elena Diaz, Rubi (ES); Volker Friedrich, Rubi (ES); Lutz Funk, Rubi (ES); Mireia Gracia, Rubi (ES); Yolanda Marquez, Rubi (ES); Pau Turón Dols, Rubi (ES)

(73) Assignee: B. Braun Surgical S.A., Rubi (ES)

( * ) Notice: Subject to any disclaimer, the term of this patent is extended or adjusted under 35 U.S.C. 154(b) by 753 days.

(21) Appl. No.: 17/434,817

(22) PCT Filed: Mar. 26, 2020

(86) PCT No.: PCT/EP2020/058509
§ 371 (c)(1),
(2) Date: Aug. 30, 2021

(87) PCT Pub. No.: WO2020/207808
PCT Pub. Date: Oct. 15, 2020

(65) Prior Publication Data
US 2022/0087675 A1    Mar. 24, 2022

(30) Foreign Application Priority Data

Apr. 12, 2019 (EP) .................... 19382284

(51) Int. Cl.
*A61B 17/06* (2006.01)
*A61B 17/00* (2006.01)

(52) U.S. Cl.
CPC ............... *A61B 17/06166* (2013.01); *A61B 2017/00526* (2013.01); *A61B 2017/06176* (2013.01)

(58) Field of Classification Search
CPC .... A61B 17/06166; A61B 2017/00526; A61B 2017/06176; A61B 2017/06057; A61B 2017/0464; A61B 17/04; A61B 2017/0412
See application file for complete search history.

(56) References Cited

U.S. PATENT DOCUMENTS 3,123,077 A    3/1964  Alcamo
5,123,913 A *  6/1992  Wilk .............. A61B 17/12009
                                            24/17 AP (Continued)

FOREIGN PATENT DOCUMENTS

AU    2013200710 B2    2/2013
CN    101518457 A      9/2009

(Continued)

OTHER PUBLICATIONS

Extended Search Report received in European Application No. 19382284.8-1122 dated Oct. 23, 2019, 8 pages.

(Continued)

*Primary Examiner* — Mohamed G Gabr
*Assistant Examiner* — Khoa Tan Le
(74) *Attorney, Agent, or Firm* — Christopher A. Rothe; CM Law (57) ABSTRACT

A wound closure device, in particular a surgical suture, includes an elongated body and projections protruding from the elongated body. Each of the projections is in the shape of a fin-like angular anchoring element having a lower base part with a base length, an upper top part, and a height. The anchoring elements are arranged in a longitudinal direction along the length of the elongated body in at least two rows with a distance between any two anchoring elements in any row. Each anchoring element in a row is aligned relative to an anchoring element of any other row, and each section of the elongated body between two successive anchoring ele- (Continued)

ments in a row has the same tapered shape in the longitudinal direction, with a steady change or an essentially steady change in the cross-sectional area of the elongated body.

20 Claims, 6 Drawing Sheets

(56) References Cited

U.S. PATENT DOCUMENTS

| | | | | |
|---|---|---|---|---|
| 5,931,855 | A | * 8/1999 | Buncke | B26D 3/08 606/228 |
| 9,713,467 | B2 | 7/2017 | Cohen et al. | |
| 9,872,679 | B2 | 1/2018 | Perkins et al. | |
| 10,952,721 | B2 | * 3/2021 | Gross | B23K 26/361 |
| 2004/0060409 | A1 | * 4/2004 | Leung | A61B 17/04 83/522.14 |
| 2005/0267531 | A1 | 12/2005 | Ruff et al. | |
| 2007/0257395 | A1 | * 11/2007 | Lindh | B29C 43/021 264/171.12 |
| 2009/0012560 | A1 | * 1/2009 | Hunter | A61B 17/06166 606/228 |
| 2009/0043336 | A1 | * 2/2009 | Yuan | A61B 17/06166 606/228 |
| 2009/0210006 | A1 | * 8/2009 | Cohen | A61B 17/06166 606/228 |
| 2011/0282384 | A1 | 11/2011 | Odermatt et al. | |
| 2012/0150194 | A1 | * 6/2012 | Odermatt | A61B 17/06166 606/228 |
| 2013/0085525 | A1 | * 4/2013 | Nawrocki | A61B 17/06166 606/228 |
| 2015/0094760 | A1 | 4/2015 | Odermatt et al. | |
| 2017/0079646 | A1 | 3/2017 | Nawrocki et al. | |
| 2020/0093483 | A1 | 3/2020 | Gross et al. | |
| 2023/0263519 | A1 | 8/2023 | Nawrocki, Sr. et al. | |

FOREIGN PATENT DOCUMENTS

| | | |
|---|---|---|
| CN | 103889340 A | 6/2014 |
| CN | 104640508 A | 5/2015 |
| CN | 104981212 A | 10/2015 |
| EP | 1075843 A1 | 2/2001 |
| EP | 1656890 A2 | 5/2006 |
| EP | 2449981 A1 | 5/2012 |
| EP | 2638863 A1 | 10/2015 |
| GB | 1091282 | 11/1967 |
| WO | 2004030704 A2 | 4/2004 |
| WO | 2005112787 A2 | 12/2005 |
| WO | 2009020795 A1 | 2/2009 |
| WO | 2013048947 A1 | 4/2013 |

OTHER PUBLICATIONS

Search Report received in International Application No. PCT/EP2020/058509 dated Jun. 18, 2020, 4 pages.
Written Opinion received in International Application No. PCT/EP2020/058509 dated Jun. 18, 2020, 6 pages.
Office Action received in Chinese Application No. 202080028338.1 dated Feb. 20, 2024, with translation, 18 pages.

* cited by examiner

WOUND CLOSURE DEVICE

CROSS-REFERENCE TO RELATED APPLICATIONS

This application is the United States national phase entry of International Application No. PCT/EP2020/058509, filed Mar. 26, 2020 and claims the benefit of priority of European Application No. 19382284.8, filed Apr. 12, 2019. The contents of International Application No. PCT/EP2020/058509 and European Application No. 19382284.8 are incorporated by reference herein in their entireties.

FIELD

This invention relates to a wound closure device, in particular to a surgical suture. This wound closure device normally comprises an elongated body having a cross-sectional area with diameter D, and projections protruding from said elongated body. As a consequence, the wound closure device according to the invention could also be named as a wound closure device with so-called barbs, in particular a barbed suture.

BACKGROUND

Wound closure devices with barbs, especially barbed sutures, have been developed for many years in order to increase the holding strength e.g. of the suture and/or to eliminate the need for knot tying. The corresponding devices have been used for closing wounds, for tissue support and for repair of internal tissues such as tendons and ligaments.

Early embodiments for barbed sutures are e.g. disclosed in U.S. Pat. No. 3,123,077 and GB-A-1,091,282. The first publication shows a surgical suture with sharp-edged, resilient barbs projecting from the elongated body of the suture in various dispositions. The second publication also shows sutures with a plurality of barbs.

EP-A2-1656890 describes a machine and method for producing a barbed suture. The corresponding machine and method can be used to produce sutures with barbs in a regular or staggered disposition.

Further barbed sutures are disclosed in EP-A1-1075843 wherein protrusions with sharpened ends are sequentially arranged along the length of the surgical thread. Preferably, the protrusions are alternated in section of from one to four positions.

In WO-A2-2004/030704, a barbed suture for connecting tissue having an elongated body and a plurality of barbs projecting from the body is disclosed. The disposition of the barbs on the body may be staggered, twist cut multiple spiral, overlapping or random.

The barbed suture disclosed in WO-A1-2009/020795 includes a shaft/body extending longitudinally along a length of the suture, and a plurality of barbs extending outwardly from said shaft. The barbs are non-symmetrical with a constant shape and diameter of the shaft between the barbs.

EP-A1-2449981 describes a barbed medical device, wherein each barb extending from the elongated body has two different cut angles, and wherein the diameter of the elongated body is constant.

Finally, in WO-A1-2013/048947, a wound closure device with a stop element coupled to the distal end of a filamentary element is disclosed. In a preferred embodiment, the wound closure device can have a plurality of projections extending outwardly from said filamentary element. This filamentary element has a constant diameter over its full length.

SUMMARY

Considering the disclosure of the above mentioned prior art, the present invention also wants to provide a wound closure device with a self-anchoring capacity, namely a wound closure device having barb elements/projections, enabling the device, in particular the suture to be pulled through tissue in one direction, but resisting movement in the opposite direction. However, in this context, the present invention has the object to provide an increased knotless wound closure capacity intended to securely fixing tissue without using knots. This improvement of the anchoring strength of the suture/device shall be provided while maintaining passage of the suture/device through biological tissues in one direction before the suture/device is anchored in the opposite direction.

Referring to what is mentioned above, the present invention discloses a wound closure device comprising an elongated body having a cross-sectional area with diameter D, and projections protruding from said elongated body, i.e. beyond the (outer) surface of said elongated body. Further, according to the invention,
- each of said projections is in the shape of a fin-like angular anchoring element having a lower base part with a base length L, an upper top part, and a height H,
- said anchoring elements are arranged in longitudinal direction along the length of the elongated body one after the other in at least two rows, with a distance G between any two anchoring elements in any row,
- each of said anchoring elements in a row is aligned relating to each corresponding anchoring element of any other row, and
- each section of the elongated body between two successive anchoring elements in a row has the same tapered shape in longitudinal direction, with a steady change or an essentially steady change in the cross-sectional area of the elongated body, and consequently a corresponding change in diameter D.

DETAILED DESCRIPTION

Figure 1:
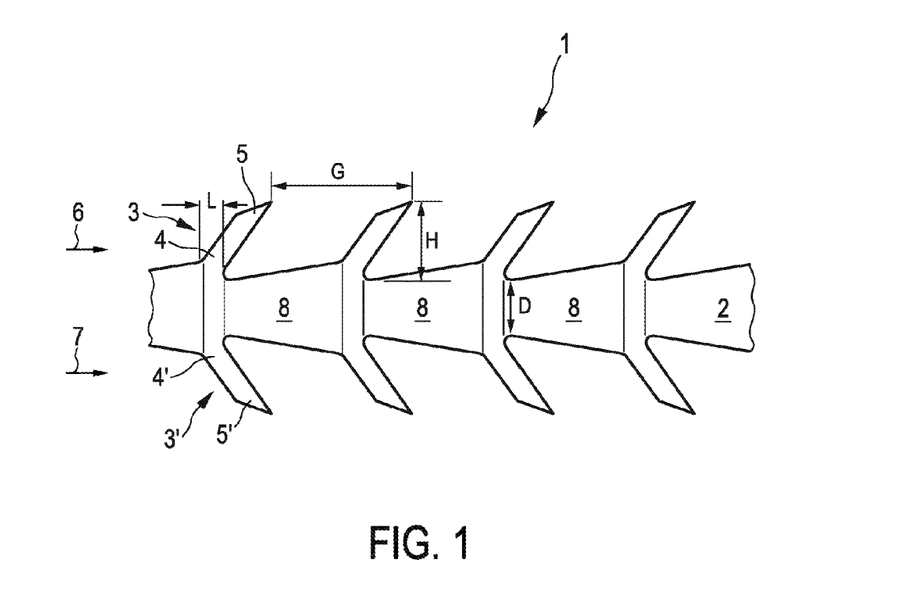
FIG. 1 is a schematic, cross-sectional view of an inventive device according to the invention, namely of an inventive surgical suture.
Figure 2:
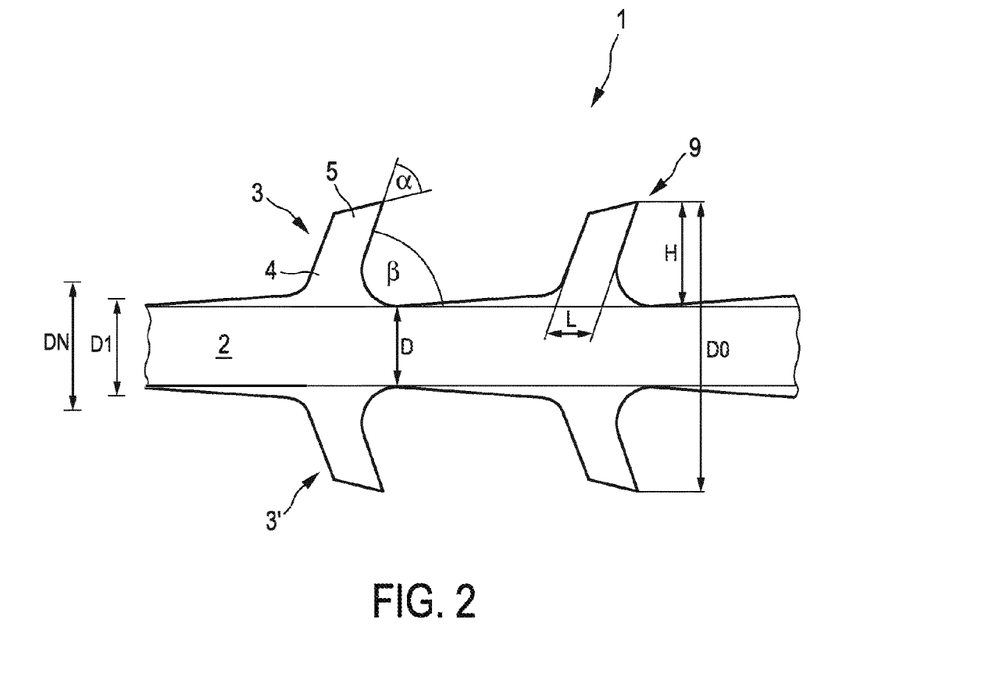
FIG. 2 is a further schematic, cross-sectional view of the inventive surgical suture.

The following explanations of the terms used to define the inventive wound closure device, can be further understood by reference to FIGS. 1 and 2. As a consequence, the disclosure of these two FIGS. 1 and 2 can be used to further clarify these explanations.

The term "fin-like angular anchoring element" is to be understood that this anchoring element essentially is in the shape of a vertical fin or vertical stabilizer of a tail unit or empennage of an aircraft. In this context, according to the present invention, opposite sides of this shape must not be necessarily parallel.

These fin-like angular anchoring elements, being the projections or barbs protruding beyond the surface of the elongated body, have a lower base part with a base length L, wherein, according to FIG. 2, this base length L is defined on the elongated body via a virtual plane on the elongated body and two parallel planes defined by the limits of the anchoring element. Further, the fin-like anchoring elements have an upper top part (see FIG. 1), and a height H. According to FIG. 2, this height H is defined via the virtual plane on the elongated body and the upper limit of the anchoring element.

In the cross-sectional area of the elongated body, a diameter D according to the present invention is defined to be the distance, in particular the smallest distance, between two opposite points on the virtual plane perpendicular to the longitudinal direction of the elongated body between successive anchoring elements. According to FIG. 2, diameter D is marked with respect to a wound closure device having two rows of anchoring elements with a rotational off-set of 180°. In this graphic representation, D is chosen to be the smallest distance in the smallest cross-sectional area of the tapered-shaped section of the elongated body between two successive anchoring elements.

In this context, it has to be mentioned that diameter D could be also defined to be an "inner diameter" of the inventive device, as this diameter D characterizes the inventive device without consideration of the anchoring elements. As it will be discussed later, one could also define an "outer diameter D0" which considers the anchoring elements protruding from the elongated body. As it can be seen from FIG. 2, said (outer) diameter D0 can be defined to be (inner) diameter D+2 height H. Clearly, this definition can vary, as e.g. according to the invention not all anchoring elements necessarily have to have the same height H.

Further, as it is shown in FIG. 1, the distance G between two adjacent anchoring elements in a row is to be understood as the distance between the outer limits of these two anchoring elements, facing into the same direction along the length of the elongated body.

As stated above, each of the anchoring elements in a row has to be aligned relating to each corresponding (opposite) anchoring element of any other row. The term "aligned" is to be understood that there is no significant deviation in the position of the corresponding anchoring elements, related to a virtual plane perpendicular to the longitudinal direction along the length of the elongated body and parallel to the cross-sectional area of the elongated body. In particular, it is preferred that in a graphic representation according to FIG. 2, base length L plotted for an anchoring element in one row must have at least an overlap with base length L plotted for each corresponding (opposite) anchoring element of any other row, which has to be "aligned" relating to the anchoring element mentioned first.

Finally, according to the invention, each section of the elongated body between two successive anchoring elements in a row has a tapered shape, i.e. this section essentially has the geometrical shape of a truncated cone. Further, this truncated cone with its tapered shape in longitudinal direction has a steady change or an essentially steady change in the cross-sectional area of the elongated body. Preferably, the smaller (top) area of said truncated cone is oriented into the longitudinal direction of the elongated body in which this body will be inserted into the tissue before anchoring (see e.g. FIG. 2).

According to the invention, each section of the elongated body between two successive anchoring elements in a row has essentially the same tapered shape in longitudinal direction (with the corresponding anchoring elements in-between). Therefore, one could also define an inventive wound closure device in a way that it is put together from the above-mentioned sections with the same tapered shape in longitudinal direction, or in the way that those sections are repeated to form the inventive wound closure device (together with the corresponding anchoring elements in-between).

While the inventive wound closure device, in particular the surgical suture can consist of several filaments, braided or twisted together, or can be a pseudo-monofilament (braided or twisted core with sleeve), it is preferred to be a monofilament, i.e. it consists of only one thread-like structure.

As disclosed above, according to the present invention, there have to be at least two rows of anchoring elements in longitudinal direction along the length of the elongated body, wherein said anchoring elements in a row are aligned relating to each corresponding anchoring element of any other row. As a consequence, it is possible to provide e.g. three rows or four rows of anchoring elements on the elongated body.

Nevertheless, in preferred embodiments of the present invention it is preferred to provide two rows of anchoring elements protruding from said elongated body. While it is possible to rotationally off-set (space apart from each other) those two rows in any reasonable angle, e.g. by 90° or 120°, it is preferred that these two rows have a rotational off-set of 180° from each other with regard to the longitudinal axis of the elongated body. With this disposition of the anchoring elements in these two rows, the anchoring strength of the device, in particular the suture, is improved.

As defined above and also referring to FIG. 2, the fin-like angular anchoring elements in the inventive device can be described to have the shape of the vertical fin of an aircraft empennage. In this context, it can also be said that in a preferred embodiment of the inventive device, said anchoring elements have a trapezoidal shape. This trapezoidal shape is to be considered in a side view onto the anchoring element.

It is further preferred according to the invention that the anchoring elements have an arch-like shape, wherein preferably said anchoring elements have an arched upper top part. Preferred features of these anchoring elements will be explained in further detail in context with the drawings. The arched contact area of the anchoring element, in particular of its upper top part, allows an improved anchoring of the anchoring elements in tissue.

Further, it is preferred according to the invention, that the anchoring elements have at least one pointed edge at their upper top part, preferably at their arched upper top part. In the latter case preferably an arched pointed edge on each anchoring element is provided, which runs along the upper top part of each anchoring element. As it will be explained later in context with the drawings, this pointed edge improves significantly the anchoring strength of the device in biological tissues.

The superior anchoring effect of the inventive suture is related to the characteristic open geometry of the inventive surgical suture with anchoring elements having fin-like angular shape, resulting in that the main contact in-between suture-tissue mainly occurs in the preferably arched upper top part of the anchoring element.

The pointed edge as mentioned above can be defined preferably in a sectional view, e.g. as explained e.g. in FIG. 2, by a point angle α. Preferably, said point angle α can be 70°, wherein it is preferred that the point angle α is between 15° and 60°. Within this latter range, point angles between 20° and 55° are further preferred.

Referring now to the inclination of the anchoring elements relating to the surface of the elongated body an inclination angle β can be defined (see FIG. 2), namely between a virtual plane on the elongated body and the corresponding plane defined by the (interior) limit of the anchoring element. In this context, it is possible to provide the anchoring elements with an inclination angle β of 90° between said anchoring element and said surface. In these embodiments, the anchoring elements will protrude from the longitudinal body vertically. However, as it is beneficial for a (smooth) passage of the inventive device through biological tissues (in one direction), inclination angles β 85° are preferred. With these embodiments, the anchoring elements, where appropriate, could give way or can even (slightly) bend in direction to the surface of the elongated body. In this context, inclination angles β between 20° and 80° are preferred, wherein in this range inclination angles β between 20° and 75° are further preferred. Also preferred are inclination angles β between 35° and 65°.

According to the invention, not all anchoring elements in a row must have the same height H. In principle, it is possible to choose the height H of the anchoring elements in a row randomly or in a specific, e.g. alternating order. Nevertheless, it is preferred, that all anchoring elements in a row have the same height H. This choice of the same height H has also advantages in the production of the inventive device which will be explained later.

In view of the above discussion of the height H relating to the anchoring elements in one row, it is also preferred that the anchoring elements in all rows on the elongated body have the same height H.

Also, with respect to the distance G between any two anchoring elements in any row it is possible to choose different distances G between two anchoring elements in a row. In this context, it is also possible to choose this distance G randomly or in a specific order, e.g. in an alternating order. Nevertheless, in particular due to the easier manufacturability, it is preferred that distance G between any two anchoring elements in a row is constant.

In order to optimize the inventive device by maintaining an easy passage of the device through biological tissue in one direction while improving significantly the anchoring strength of the device in the opposite direction, it is preferred to choose specific ratios between diameter D, related to the cross-sectional area of the elongated body, and above-mentioned parameters, namely height H and distance G. Further, specific ratios between base length L and distance G can be of advantage. For determining these ratios, diameter D, height H, distance G and base length L are determined as explained above in context with FIGS. 1 and 2.

As a consequence, preferred embodiments of the invention are defined by a ratio between diameter D and height H from 1:0.3 to 1:5, in particular from 1:0.8 to 1:3. Within the latter range, ratios D:H from 1:1 to 1:2 are further preferred.

Further, ratios between diameter D and distance G from 1:0.8 to 1:15, in particular from 1:1 to 1:10, are preferred. Within the latter range, ratios D:G from 1:1.5 to 1:6 are further preferred.

Relating to the ratio between base length L and distance G, values for these ratios from 1:0.8 to 1:6, in particular from 1:1 to 1:3, are preferred.

As already mentioned it is preferred according to the present invention that the new wound closure device is a surgical suture or surgical thread. Such a surgical suture is the classical example of an inventive device with an elongated body and projections protruding beyond the surface of said elongated body with the features according to the invention.

Further, it is preferred that the inventive device, in particular the inventive surgical suture, is provided in embodiments in which a majority of said anchoring elements in a row point in the same longitudinal direction along the length of said elongated body, i.e. they have the same orientation along the length of the elongated body. In this context, if pointed edges are provided at said anchoring elements, it is further preferred that also a majority of said pointed edges point in the same longitudinal direction along the length of said elongated body.

Referring to the preferred embodiments mentioned above, it is further preferred that all said anchoring elements in a row, in particular also all said pointed edges of said anchoring elements, point in the same longitudinal direction along the length of said elongated body.

If a majority of the anchoring elements and possibly of their pointed edges point in the same longitudinal direction, it is understandable that a passage of the device through the tissue is possible in one direction, while the device resists movement in the opposite direction. This effect is even higher if not only a majority of said anchoring elements/pointed edges, but all anchoring elements/pointed edges point in the same longitudinal direction along the length of the elongated body.

In this context it is also understandable that this effect is even much higher, if a majority of the anchoring elements or pointed edges of all rows, or even all anchoring elements or pointed edges of all rows point in the same longitudinal direction, which refers to further preferred embodiments of the inventive device.

If a majority or all anchoring elements/pointed edges of a row or preferably of all rows have the same orientation, i.e. point in the same longitudinal direction, the wound closure device, in particular the surgical suture, can be designated to be an "unidirectional" or "monodirectional" barbed device or suture.

With other embodiments of the inventive device there are at least two portions of an elongated body with anchoring elements, wherein preferably said anchoring elements of said two portions, and in particular also said pointed edges of said anchoring elements, point in opposite longitudinal directions along the length of said elongated body. Inventive devices according to these embodiments resist movement of the device in the tissue in opposite directions so that there are flexible applications for those inventive devices. If there are two portions of an elongated body with anchoring elements pointing in opposite longitudinal directions, the corresponding device or suture can be designated to be a "bidirectional" barbed device or suture.

According to the invention, it is also possible to provide with the inventive device or suture at least one portion of an elongated body without projections. As a consequence, there are portions of the device with the inventive function of a barbed device or suture, and portions of the device without that function. Therefore, anchoring elements are only provided in those parts along the length of the elongated body in which the function of the anchoring elements/barbs is desired. For example, those portions without projections can be provided between portions with projections pointing in opposite longitudinal directions.

With the last mentioned embodiments it is further preferred that said portions of the elongated body without projections are provided at at least one (very) end of said elongated body, in particular at the end of said surgical suture. Normally, at that (very) ends, at least one pointed end or needle is provided to enable the entry of the device or suture into biological tissue and/or the passage of the device or suture through biological tissue.

Preferably, in the embodiments of the inventive device mentioned above with portions of an elongated body without projections, those portions without projections have a diameter D1 representing the cross-sectional area of said portion, which is different from, in particular greater than (inner) diameter D representing the cross-sectional area of an elongated body with anchoring elements.

According to the invention, in preferred embodiments, the wound closure device, in particular the surgical suture, comprises at least one pointed end, in particular a surgical needle, at at least one end of said elongated body. This end of said elongated body with the pointed end or surgical needle is opposite to the orientation of the corresponding anchoring elements, i.e. to the longitudinal direction in which the corresponding anchoring elements (and possibly also the pointed edges of said anchoring elements) point. Preferably, said pointed end or surgical needle is provided at a portion of the elongated body without projections, wherein said portion without projections preferably has a diameter D1 greater than diameter D of the elongated body with projections/anchoring elements.

Referring to the above-mentioned embodiments, an unidirectional or monodirectional barbed device or suture can be provided with a pointed end or surgical needle at one (proximal) end of the elongated body and with anchoring elements pointing into the longitudinal direction opposite to the direction of the end with pointed end or needle. There is also the possibility to provide a bidirectional barbed device or suture with pointed ends or surgical needles at both ends of the elongated body, with two portions of an elongated body with anchoring elements each pointing in a direction opposite to the longitudinal direction of its pointed end or needle.

The diameter of the pointed ends, in particular the diameter of the surgical needles (which is designated in the following as DN), is chosen to support the function of the inventive device, in particular of the inventive suture. In this context, on the one hand diameter DN has to be great enough that the inventive device can be inserted into tissue and guided through the tissue in one direction. On the other hand, with the present invention the anchoring capacity is, contrary to surgical sutures known from the prior art, not so related to or limited by the incision channel and guiding channel that the pointed ends, in particular the surgical needles provoke in tissue. Due to the advantageous design of the inventive wound closure device, in particular of the inventive surgical suture, with its anchoring elements having a fin-like angular shape, a strong contact between the walls of the incision and guiding channel and the anchoring elements of the inventive device is possible. This is particularly true, if the preferred features and ratios mentioned herein are fulfilled. In these cases, the anchoring elements of the inventive device are particularly prominent and firm, resulting in a very strong interaction between the inventive device with its anchoring elements and the tissue in which this device is used.

As a consequence, it is not only possible to use surgical needles with the present invention having a diameter DN which is larger than or equal to the (outer) diameter D0 of the inventive surgical suture (as it is also the case with barbed sutures known from the prior art). According to the present invention it is also possible, and even preferred to choose a diameter DN of the surgical needle which is smaller than the (outer) diameter D0 of the inventive surgical suture (D0≥DN). Due to the specific design of the inventive surgical suture also in these cases a full anchoring capacity can be provided in the tissue.

Specific ratios between diameter DN and D0 from 1:0.70 to 1:1.70, preferably 1:0.75 to 1:1.60, in particular from 1:0.80 to 1:1.40 are further preferred.

According to the invention, preferably the elongated body and the projections, i.e. the anchoring elements, are made from the same material. According to these embodiments the whole wound closure device, in particular the whole surgical suture, preferably in the form of a monofilament, essentially consists of the corresponding material (possibly with the exception of any pointed ends, e.g. surgical needles, and/or any stopping elements and/or any additives or active agents).

The material for the inventive device can in principle be chosen from all materials already used in the field, in particular for surgical sutures, in particular from polymers. The polymers can be resorbable polymers or non-resorbable polymers or partially resorbable polymers. Examples of polymers that can be used are homopolymers, copolymers, terpolymers or tetrapolymers, etc. Suitable polymers are, for example, block polymers, in particular block copolymers or block terpolymers, or graft polymers. The use of arbitrary or random or alternating copolymers or terpolymers is also possible according to the invention.

In a preferred embodiment, the used material is made from a resorbable polymer from the group including polylactide, polyglycolide, poly-ε-caprolactone, poly-para-dioxanone, polytrimethylene carbonate, polyhydroxybutyric acid, mixtures thereof, copolymers thereof and terpolmyers thereof. The used material is also preferably made from a resorbable copolymer or terpolymer which comprises at least one monomer from the group including lactide, glycolide, trimethylene carbonate, para-dioxanone and ε-caprolactone. For example, the material used for the invention can be made from a terpolymer, preferably a triblock terpolymer, comprising glycolide, trimethylene carbonate and ε-caprolactone.

The non-resorbable materials can be polymers, metals, metal alloys or natural fibers, for example silk or cotton. However, in this embodiment, non-resorbable polymers are preferred, particularly from the group including polyolefins, polyesters, polyamides, polyurethanes, mixtures thereof, copolymers thereof and terpolymers thereof. For example, the material according to the invention can be formed from polypropylene, polyethylene terephthalate, a linear and preferably aliphatic polyurethane, polytetrafluoroethylene and/or nylon.

In further preferred embodiments, the used material comprises at least one additive as an active agent. Said additives can be part of the corresponding material, e.g. they can be blended or mixed to this material. However, it is also possible that these additives are provided in the form of a coating or layer on the material, e.g. on the surfaces of the elongated body and/or projections. Preferably, the used material comprises additives selected from the group consisting of biological agents, medical agents, pharmaceutical agents, cells, and/or combinations thereof.

Biologically active agents are preferably differentiation factors, growth factors, recruiting factors and/or adhesion factors. Appropriate growth factors may be selected from the group consisting of fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insuline-like growth factors (IGF), hepatocyte growth factor (HGF), interleucin-1 B (IL-1 B), interleucin-8 (IL-8), nerve growth factor (NGF), and combinations thereof.

Medical and/or pharmaceutical agents may be antimicrobial agents, in particular antibiotic agents, disinfecting agents, oncological agents, wound-healing agents, anti-scarring agents, pain-killing agents, growth-promoting agents, anti-inflammatory agents, analgetic agents and/or odor-controlling agents.

Suitable antimicrobial agents may be selected from the group consisting of biguanide, chlorhexidine diacetate (CHD), polyhexamethylene biguanide (PHMB), triclosan, gentamycin, copper, zinc, silver, gold, salts thereof, stereoisomers thereof, and combinations thereof.

A preferred anti-scarring agent may be an angiotensin I enzyme inhibitor such as captopril.

Preferred cellular additives may be somatic cells, in particular autologous cells like fibroblasts, chondrocytes and or precursor cells, in particular stem cells, for example. A cellular additive to the material is advantageous in that substances produced and secreted by the cells may be an aid in accelerating wound healing, for example.

Furthermore, substances, like collagen and/or hyaluronic acid for example, may be particularly beneficial in plastic surgery to achieve cosmetically satisfactory results, like a smoothing of wrinkles, for example.

The inventive wound closure device, in particular the inventive surgical suture, can be produced according to different methods, e.g. by cutting methods or by molding methods (from melt or solution, injection molding, compression molding and others). Stamping, drilling, lasering and overmolding are also possible methods.

However, it is preferred that the inventive device, in particular the inventive suture is produced according to an inventive method in which
1. an undrawn elongated body, preferably a monofilament is pre-stretched along its longitudinal direction (along its length),
2. cuts are made into the pre-stretched elongated body, and then
3. this pre-stretched elongated body with cuts is stretched or drawn (apart) in its longitudinal direction, in order to form the inventive surgical suture with the anchoring elements according to the invention. After this stretching step the elongated body has a diameter D1 in any portions, where no cuts have been provided according to step 2., and a diameter D in all portions, where cuts have been provided according to step 2.

The undrawn elongated suture, preferably provided in the form of a monofilament preferably has a circular or oval cross-sectional area. However, it is also possible to provide a suture with other cross-sectional shapes. For example, the suture can have triangular, square, trapezoidal, rhomboid, pentagonal, hexagonal, star-shaped or cross-shaped area as a cross-section. Such shapes can be e.g. easily formed with the aid of extrusion dies, which can be provided with any desired cross-sectional shape for the extruded bodies.

On the one hand the pre-stretching step serves to straighten the fiber and to remove the memory of the thread caused by the round shape of the spool the fiber was wound on after the extrusion. On the other hand it is advantageous to prepare the fiber for the following cutting process, because during the pre-stretching the fiber and its surface get more rigid. It is assumed that this change of rigidity of the fiber is due to the alignment/crystallization of the polymer chains during pre-stretching.

During the cutting step, for each anchoring element which is later present in the inventive device, namely on the corresponding elongated body, exactly one cut has to be provided. As a consequence, in order to provide projections for the inventive device which are arranged one after the other in at least two rows, it is necessary in the cutting step to provide cuts for each projection in the at least two rows. If, according to the invention, a preferred arrangement of projections in two rows with a rotational off-set of 180° is to be provided, in the second production step cuts have to be provided in two rows with a rotational off-set of 180°. All these cuts can be provided one by one, or simultaneously in groups, or simultaneously all cuts together. E.g. all cuts in a row can be made simultaneously.

In this context it has to be mentioned, that with the inventive method, under normal circumstances during the cutting process no projections protruding above the surface of the material will be present. The cutting process will simply result in a cut, but not in a projection.

In order to produce the inventive device, in particular the inventive suture, it is preferred that in the second step the cuts are placed in an angle≤70°, preferably between 15° and 60°, in particular between 20° and 55°, with regard to the longitudinal axis of the monofilament.

With regard to the diameter of the undrawn elongated body (starting material of step 1.) it is preferred that the cuts are provided with a depth of between 5% and 50%, in particular between 25% and 45%, of this diameter.

The cuts can be provided mechanically, preferably by using at least one cutting blade. In this context, it is possible to use only one blade, e.g. to provide all cuts in one row, and then to provide the corresponding cuts in (at least) another row. Nevertheless, it is also possible to use two or more blades, in order to provide (aligned) cuts in at least two rows simultaneously. In all these cutting processes either the blade(s) or the suture can be moved in order to bring the blade(s) to the position of the next cut(s).

The projection which protrudes from the material is provided by the above mentioned third step, namely the stretching/drawing step in which the suture material, preferably the pre-stretched monofilament (with the cuts) is pulled (apart). In this step, the e.g. pre-stretched monofilament material is further stretched/elongated whereby the fin-like angular elements according to the invention protrude. Simultaneously the sections with a tapered shape in longitudinal direction according to the invention are formed. After the second (cutting) step, the suture, in particular the monofilament material (with cuts) is brought in its drawn state. This is done by pulling the material in at least a part of its length apart. In this third step the material is elongated and simultaneously the fin-like angular anchoring elements raise beyond the surface of the elongated body. Also the corresponding sections between two successive anchoring elements with tapered shape are formed.

The drawing step can be preferably done with the application of heat, depending on the material, in particular polymer material, from which the monofilament is made. The usual temperature range for the drawing step is between 20° C. and 150° C.

Further, the inventive wound closure device, in particular the inventive (unidirectional) surgical suture, preferably can comprise at least one stopping element at the end of said elongated body which is in the longitudinal direction in which the anchoring elements and possibly also the pointed edges of said anchoring elements point. The stopping element has the function to further fix the position of the device in the tissue or relating to the tissue after the device has been anchored in the tissue via the anchoring elements provided on the elongated body of the device. As a consequence said stopping elements can be also named fixation elements or locking elements or fixation effectors or end effectors or the like. E.g. a variety of stopping elements known from the prior art is disclosed in WO-A2-2005/112787.

Among others, the stopping element used according to the invention can be in the form of a (small) bar, a (small) tab, a (small) plate or a (small) stripe. With all these embodiments the corresponding stopping element extends (or is able to extend during use) radially outwardly of the elongated body in a plane substantially perpendicular to the longitudinal axis of the elongated body. For enhancing its function the stopping element can comprise additional features like additional self-gripping elements (e.g. rake-like stopping element).

Further embodiments of stopping elements which can be used according to the invention include a loop, a double loop, a sliding loop, or a sliding knot. Other embodiments include a (short) bidirectional barbed segment as a stopping element or a bulbus as a stopping element.

Other stopping elements which can be also used according to the invention include structures which can be transferred during use from an unzipped to a zipped configuration. These are configurations with a zig-zag-locking design or with a spring locking design.

Also tubular constructions are possible as a stopping element wherein e.g. an initially tubular element is locked during use of the surgical suture to a flat element blocking further motion of a suture.

According to the present invention, use of a stopping element in the form of a flat tab is preferred. Together with the elongated body of the surgical suture such a tab gives the suture with stopping element a so called "T-shape". The surgical suture with these stopping elements in the form of a tab can also be transferred into this "T-shape" design when the surgical suture is anchored in the tissue. This will be explained later in connection with the drawings.

The stopping elements in the form of a tab can have a circular shape, an oval shape or an angular shape. With angular tabs it is preferred that the edges of these angular tabs (triangle, rectangle, square or the like) are rounded in order to avoid any unnecessary damage of tissue.

Depending on the actual design of the tab-like stopping elements the maximum dimensions of these stopping elements (length, width, diameter) preferably do not exceed 4.5 mm, and are preferably ≤3.5 mm. E.g. with a rectangular tab-like stopping element the larger dimension in the plane of the tab is preferably ≤4 mm, in particular between 3.5 mm and 2.5 mm, and the smaller dimension is ≤3.5 mm, in particular between 2 mm and 1 mm.

The thickness of the tab used as a stopping element does preferably not exceed 0.4 mm. Preferably said thickness is ≤0.3 mm, preferably between 0.2 mm and 0.1 mm.

The stopping element which can be used according to the invention can be made of any suitable material which is already used in the field as a material for surgical sutures. Therefore, any of the suture materials and structures which are discussed above can be used to construct the stopping elements discussed in this description.

It is further preferred that the stopping element used together with a surgical suture is made from the same material as the material for the surgical suture.

The methods for producing the stopping elements according to the present disclosure are within the purview of those skilled in the art and include, but are not limited to, stamping, die cutting, drilling, lasering, molding (melt, solution, injection, compression, etc.) and overmolding. Also, stopping elements may be constructed by glues, adhesives, ultrasonic welding or heat welding, or other methods as selected by one of ordinary skill in the art.

Further advantages and features of the invention will become clear from the following description of the example and of the drawings. The individual features can be realized either individually or in combination in a corresponding embodiment of the invention. The drawings merely serve for illustration and better understanding of the invention and are not to be understood as in any way limiting the invention.

Example 1

Manufacturing of an Inventive Surgical Suture
Step 1: Extrusion

Polyglyconate granulate was dried for 18 h at 70° C. in a vacuum at a pressure of <$10^{-1}$ mbar before the extrusion. The extrusion was performed on a BERSTORFF® brand twin-screw extruder manufactured by KrausMaffei Technologies GmbH (temperature profile 205° C., 215° C., 215° C.) connected to a melt pump (215° C., 0.25 ccm/rotation, 17.7 rpm (nominal value), die pressure 130±30 bar) to ensure a homogenous flow of the polymer melt through the monofilament die and therefore a homogeneous diameter of the resulting monofilament. After passing through the die, the resulting fiber is quenched in a water bath (44° C.±2° C.) and passed over motorized godets/rollers (speed of 10 rpm) to be finally wound in one layer on cylindrical spools made of metal. The resulting monofilament had an average diameter of 0.645±0.010 mm. The monofilament fiber remained 5 h at 18° C. on the metal spools for crystallization and received then a post-treatment for 3 h at 40° C. applying a vacuum of <10 mbar.

Step 2: Pre-Stretching

An undrawn (not stretched) polyglyconate monofilament as provided in step 1 was cut to pieces having a length of approximately 60 cm and then fixed to the clamps of an automatic drawing oven at distance of 460 mm. Pre-stretching of the monofilament with a ratio of 1:1.84 was then performed in the drawing oven at a temperature of 120±2° C. and at a drawing speed of 5 mm/s.

Step 3: Cutting of the Pre-Stretched Monofilament

The pre-stretched polyglyconate monofilament pieces as provided in step 2 were fixed at their ends to the clamps of the cutting machine and held there at certain tension. The cutting machine is equipped with different cutting modules which sequentially cut through the surface of the monofilament, thread piece is rotated 180° by clamps and cut again with the same cutting depth than the first one. In this way, identical cuts are in aligned disposition in two rows along the monofilament piece. There are two different operational setups depending on the configuration of the final product: unidirectional and bidirectional.

In order to obtain an unidirectional configuration, just one cutting module provided with a blade is used. As an example, a cutting angle of 40° and spacing between the cuts was selected to be 0.20 mm. A total number of 736 cuts were done into the undrawn monofilament fiber.

For a bidirectional configuration, two symmetrical cutting modules provided with two blades are used. Each cutting unit performs one of the two groups of cuts disposed in the bidirectional configuration of the final product. A cutting angle of 40° and spacing between the cuts was selected to be 0.20 mm. The two cutting units performed 736 cuts each one. In this way, cuts are disposed in two groups that face each other in opposing direction from the device center transition zone without cuts.

During step 3 only cuts into the monofilament material are provided. These cuts do not result in anchoring elements projecting beyond the surface of the monofilament. These anchoring elements are formed in step 4.

Step 4: Stretching/Drawing

To convert the obtained pre-stretched and cut polyglyconate monofilament pieces as provided in step 3 into a self anchoring device, these pieces were fixed to the clamps of the drawing oven and stretched at a temperature of 120° C.±2° C. and a drawing speed of 5 mm/s applying a stretching ratio of 2:1.

During said stretching step the anchoring elements according to the invention with their fin-like angular shape and their characteristic tapered section between two successive anchoring elements in a row are formed.

The resulting wound closure device had an average length of the section with projections of 14.7 cm and the average diameter of the device in the section without projections was approximately 0.370 mm. The final stretched product produced by mentioned procedure was characterized by an internal (inner) diameter (D) of 155±17 μm, a base length (L) of 141±6 μm, a height (H) of 182±13 μm, a distance between two anchoring elements (G) of 455±26 μm and angles defined as (α) and (β) with approximated values of 45° and 57°, respectively.

Example 2

Manufacturing of a Stopping Element and of a Surgical Suture with Stopping Element Step 1: Extrusion Polyglyconate granulate was dried for 18 h (overnight) at 70° C. The extrusion was performed on a screw extruder (temperature profile 206° C., 206° C., 205° C., 204° C.) connected to a melt pump (12.5 rpm) equipped to a flat-shaped die (210° C.). After passing through the die, the resulting tape was quenched in a water bath (40° C.) and passed over the first set of motorized godets/rollers (speed of 4.8 m/min). Then, the resulting tape was passed through water bath (30° C.) and following to the second set of motorized godets/rollers (26 m/min). The relation between the speed of the first and second set of godets/rollers allows to apply a draw ratio of 6.5 to the resulting tape. The stretching step confers an oriented crystallization to the resulting tape, leading to an appropriate resistance. After this stretching step, the tape was air-cooled at two furnaces and passed over the last set of godets/rollers (31 m/min) to be finally wound in one layer cylindrical spools made of metal. The tape remained 24 h at 18° C. on the metal spool to complete the crystallization process. Resulting tape had average value for thickness and width of 0.17 mm and 3.794 mm, respectively. Also, it was characterized by average values for resistance and elongation of 190 N±14 N and 39%±5%, respectively.

Step 2: Welding and Die Cutting

A surgical suture according to the invention (e.g. manufactured according to Example 1), in particular with a unidirectional configuration of its anchoring elements was provided. This suture and the tape manufactured in Step 1 were fixed by flanges on the guide lines of a platform in order to couple them by ultrasound welding technology. This technology was performed on equipment distributed under the federally registered trademark SONOTRONIC ULTRASONICS TECHNOLOGY® (Titanium sonotrode, 35 kHz). Distance between the sonotrode and the platform was adjusted to 0.29 mm and the welding time applied was 0.13 s. As a result, the tape was welded at the distal end of the barbed thread.

The die cutting process was performed on a punch press machine with its die set specifically designed to obtain the required dimensions and shape (here: 3.0 mm length and 1.5 mm width, round edges) of the stopping element. Suture with tape was inserted carefully through the die until the tape was placed correctly on the guide. Once the welding was centered at the die, a hand-press was exerted, forcing the punch through the material into the die. Finally, the (unidirectional configuration) suture with stopping element was obtained.

Example 3

Determining of Anchoring Forces in an Inventive Surgical Suture and in an Already Commercial Available Barbed Suture In the following the particular anchoring forces of the inventive surgical suture are shown in comparison to an already commercially available barbed suture.

In this context, an unidirectional surgical suture according to the invention is manufactured according to Example 1. This suture is provided for a measurement of anchoring forces (together with a needle but without any stopping element).

The parameters of the inventive surgical suture are summarized in Table 1 below.

TABLE 1

| Size | G (μm) | D (μm) | D0 (μm) | α (°) | D1 (mm) | H (μm) | L (μm) | β (°) |
|---|---|---|---|---|---|---|---|---|
| 0 | 565.2 | 230.5 | 901.8 | 39.9 | 0.714 | 349.1 | 175.3 | 50.3 |
| 2/0 | 569.2 | 196.4 | 745.8 | 40.7 | 0.580 | 275.4 | 171.2 | 54.1 |
| 3/0 | 580.7 | 163.4 | 681.2 | 42.5 | 0.514 | 255.8 | 174.1 | 56.4 |
| 4/0 | 436.5 | 158.6 | 493.7 | 45.3 | 0.380 | 180.1 | 156.8 | 58.8 |
| 5/0 | 295.3 | 143.6 | 395.1 | 43.7 | 0.309 | 127.7 | 109.6 | 56.5 |

Note that size designation in the inventive surgical suture is not directly related to the diameter of the device, but it is based on its lineal pull tensile strength, that results equivalent to knot pull tensile strength of a synthetic absorbable suture with the same USP size designation.

All the data included in Table 1 for the corresponding parameters result from a considerable number of independent measurements, namely from at least 30 measurements.

Further, another commercial suture with barbs, namely a knotless tissue-closure device distributed under the trademarks QUILL™ and MONODERM™ is also provided for such a measurement. Bidirectional barbed sutures sold under the trademarks QUILL™ and MONODERM™ are manufactured from monofilament fibers via a micromachining method cutting barbs into the suture around the circumference in a helical configuration. The barbs are separated from one another by a measured length of 0.62 to 1.39 mm, resulting in the anchoring of tissue at approximately 1 mm intervals (see Table 2 below).

The inventive surgical suture and the commercial suture with barbs, i.e. knotless tissue-closure device distributed under the trademarks QUILL™ and MONODERM™, tested to evaluate the anchoring force are characterized by a 15 cm length.

The number of anchoring elements per mm are shown in the following Table 2:

TABLE 2

| Polyglyconate Wound Closure Device according to the invention | | | QUILL ™ MONODERM ™ | | |
|---|---|---|---|---|---|
| Size | G (µm) | Anchoring elements per mm | USP | G (µm) | Anchoring elements per mm |
| 0 | 565.2 | 3.54 | 0 | 1146.3 | 0.87 |
| 2/0 | 569.2 | 3.51 | 2/0 | 1385.6 | 0.72 |
| 3/0 | 580.7 | 3.44 | 3/0 | 1363.6 | 0.73 |
| 4/0 | 436.5 | 4.58 | 4/0 | 619.5 | 1.61 |
| 5/0 | 295.3 | 6.77 | 5/0 | 636.4 | 1.57 |

The comparative measurements of the anchoring forces are performed as follows.

The corresponding surgical suture is passed through a fleece textile, wherein this fleece textile was initially folded once and then the surgical suture is sticked through the compact part of the textile with a straight needle. Then, the textile is unfolded, resulting in a flat textile enclosing approximately 2 cm of the surgical suture with the corresponding anchoring elements in unidirectional arrangement within the body of the fleece.

After fixing the corresponding suture, the Pull-Out-Force is measured in a corresponding apparatus, namely a dynamometer equipped with a load cell suitable for the corresponding force levels. Measured is the force which is needed to pull out the suture against the opposite direction the barbs point, until failure occurred or until the suture slipped through the fleece textile.

The results of the corresponding measurements are shown in Table 3

TABLE 3

| Polyglyconate Wound Closure Device according to the invention | | | | | | QUILL ™ MONODERM ™ | | | | | |
|---|---|---|---|---|---|---|---|---|---|---|---|
| Size | n | $x_i$ min | $x_{ave}$ | $x_{i\ max}$ | St.dev. | USP | n | $x_i$ min | $x_{ave}$ | $x_{i\ max}$ | St.dev. |
| 0 | 122 | 33.2 | 40.6 | 48.2 | 3.0 | 0 | 60 | 3.3 | 7.7 | 14.0 | 2.5 |
| 2/0 | 119 | 23.8 | 29.3 | 33.0 | 2.0 | 2/0 | 60 | 3.6 | 5.8 | 8.1 | 1.1 |
| 3/0 | 121 | 17.5 | 21.9 | 26.4 | 1.6 | 3/0 | 60 | 2.2 | 5.3 | 10.5 | 1.8 |
| 4/0 | 133 | 9.9 | 12.9 | 15.3 | 1.0 | 4/0 | 60 | 1.8 | 4.7 | 8.2 | 1.6 |
| 5/0 | 123 | 6.9 | 9.2 | 12.1 | 1.0 | 5/0 | 60 | 1.4 | 2.8 | 4.8 | 0.8 |

In this Table 3 the designations are as follows:
USP: United States Pharmacopeia
n: number of measurements
x: force (in Newton, with an average value (ave) and a minimum (min) and maximum (max) value)
St.dev.: Standard Deviation Table 3 shows that the inventive surgical suture has considerably higher anchoring strength compared to another commercially available barbed suture. Depending on the inventive surgical suture size its anchoring strength is between approximately 3 times to approximately 5 times higher than that of the commercially available barbed suture having the same USP designation.

According to FIG. 1 an inventive wound closure device, namely an inventive surgical suture 1, comprises an elongated body 2 and projections protruding from elongated body 2, wherein said projections have the shape of fin-like angular anchoring elements 3, 3'.

Elongated body 2 and anchoring elements 3, 3' are made from the same material, namely a material which can be used for surgical sutures, e.g. resorbable polymers, non-resorbable polymers or partially resorbable polymers.

Anchoring elements 3, 3' are arranged with the same orientation in longitudinal direction along the length of elongated body 2 one after the other in two rows 6, 7, wherein said rows 6, 7 have a rotational off-set of 180° from each other with regard to the longitudinal axis of elongated body 2.

Further, according to FIG. 1, each of said anchoring elements 3 in row 6 is aligned relating to each corresponding anchoring element 3' of the other row 7. Therefore, distance G between any two anchoring elements 3, 3' in rows 6, 7 is constant.

Each of said anchoring elements 3, 3' of surgical suture 1 has a lower base part 4, 4' with a base length L, an upper top part 5, 5', and a height H.

It can be seen already from FIG. 1 that each anchoring element 3, 3' is angular, and that each anchoring element has a fin-like shape similar to the shape of a vertical fin or vertical stabilizer of a tail unit of an aircraft. This fin-like angular shape of the anchoring elements 3, 3' provided in the inventive surgical suture is an important feature for the superior anchoring function of the inventive surgical suture.

As it is further shown in FIG. 1, elongated body 2 is characterized by diameter D of its cross-sectional area. This feature will be explained in more detail in context with FIG. 2.

Further, according to FIG. 1, elongated body 2 is characterized by the fact that each section 8 of the elongated body 2 between any two successive anchoring elements 3 in a row 6 (which are aligned with the corresponding anchoring elements 3' of the other row 7) has the same tapered shape in longitudinal direction of the elongated body 2. This tapered shape comprises a steady change or an essentially steady change in the cross-sectional area of the elongated body 2. The smaller (top) area of each section 8 is oriented to the left side of FIG. 1, namely to the direction in which suture 1 will be inserted into tissue.

In other words: The inventive surgical suture 1 shown in FIG. 1 can also be defined to be put together from a number of sections 8 with the same tapered shape in longitudinal direction, wherein between each two corresponding sections the corresponding anchoring elements 3, 3' are provided in between.

In FIG. 2 some features and parameters, already shown and explained relating to FIG. 1, are shown and explained in more detail.

Again, an inventive surgical suture 1 with an elongated body 2 and fin-like angular anchoring elements 3, 3' is shown. In this context, FIG. 2 only shows two anchoring elements 3 and 3' of each of the two rows which are rotationally off-set from each other with regard to the longitudinal axis of elongated body 2.

Each anchoring element 3, 3' has a lower base part 4, 4' with a base length L, an upper top part 5, 5', and a height H. As it was already shown in FIG. 1, all anchoring elements 3, 3' have the same fin-like angular shape with the same height H. In this context, height H is defined via a virtual plane on the elongated body and via the upper limit (top) of the corresponding anchoring element.

Further, each anchoring element 3, 3' has an inclination angle β which is defined between the virtual plane on the elongated body (see definition of height H) and the corresponding (inner) plane defined by the corresponding limit of the anchoring element (see FIG. 2).

Each anchoring element 3, 3' has a lower base part 4, 4' with essentially the same base length L. As already discussed, it is a critical feature of the invention that each anchoring element 3 in a row 6 is aligned relating to each corresponding anchoring element 3' of (any other) row 7. In this context, due to the production of an inventive device, (very) small deviations in the position of the corresponding anchoring elements can be unavoidable. Therefore, as explained earlier, the term "aligned" can be defined that there must be at least an overlap in the base lengths L of any two anchoring elements 3, 3' (opposite to each other). In this context, the base length L should be defined as shown in FIG. 1, namely by the distance between the two planes which are defined by the two outer limits of the anchoring elements.

Further, as also shown in FIG. 2, each anchoring element 3, 3' has a pointed edge 9 which is the front line of the anchoring elements 3, 3' when the surgical suture 1 is anchored in the tissue. At the position of that pointed edge 9 a point angle α is defined (see FIG. 2).

As already explained in context with FIG. 1, diameter D, as also shown in FIG. 2, is a characterizing feature of the elongated body 2 in the surgical suture 1. As shown in FIG. 2, diameter D is chosen to be the diameter of the smallest cross-sectional area of the tapered-shaped section of the elongated body between two successive anchoring elements. In this context, diameter D is the (smallest) distance between two (opposite) points of this (smallest) cross-sectional area in the virtual plane perpendicular to the longitudinal direction of the elongated body.

Also shown in FIG. 2 is (outer) diameter D0 which is defined by diameter D and the heights H of two aligned anchoring elements. As according to FIG. 2 all anchoring elements 3, 3' have the same height, D0=D+2 H.

Further shown in FIG. 2, as examples, are diameters D1 (diameter of any portion of the suture without any anchoring elements) and DN (needle diameter).

In order to further clarify the explanations according to FIGS. 1 and 2, the function of surgical suture 1 is explained as follows. Surgical suture 1 with elongated body 2 and anchoring elements 3, 3' is inserted into and pulled through tissue in the same direction where the anchoring elements point out. This is done by a pointed end or surgical needle (not shown) attached to the left end of surgical suture 1 in FIGS. 1 and 2. Anchoring elements 3, 3' will anchor themselves in the tissue which surrounds the suture 1. Due to the fin-like angular shape of the anchoring elements and due to the tapered shape of the sections of the elongated body there is a superior anchoring effect of the inventive surgical suture 1.

Figure 3:
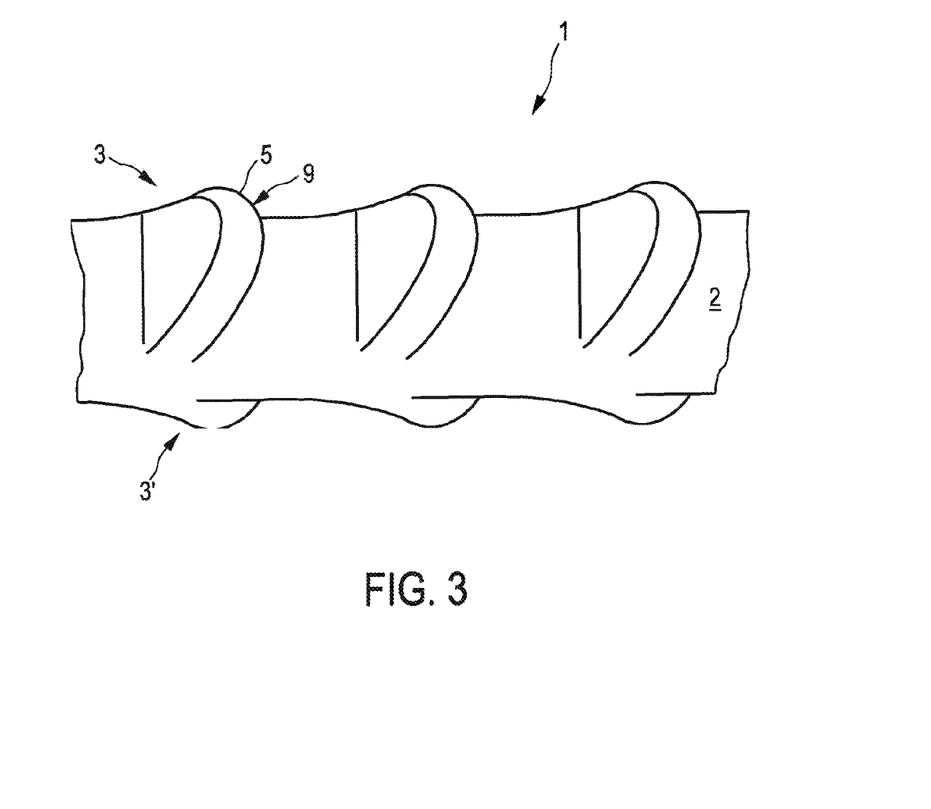
FIG. 3 is a further schematic, perspective view of the inventive surgical suture.

FIG. 3 is a (further) perspective view of an inventive surgical suture 1 already shown in FIGS. 1 and 2. FIG. 3 mainly serves to illustrate the design of the upper top part 5 of the inventive surgical suture 1.

Also according to FIG. 3 a surgical suture 1 is shown in which anchoring elements 3, 3' are arranged with the same orientation in longitudinal direction along the length of elongated body 2 one after the other in two rows, wherein the two rows have a rotational off-set of 180°.

Further, as also shown in FIG. 2, and marked in FIG. 3 with respect to anchoring element 3, each anchoring element has a pointed edge 9 which is the front line of the anchoring elements when the surgical suture 1 is anchored in the tissue. This will be further explained later in the context of FIG. 4.

It can be also clearly seen from FIG. 3 that (as earlier explained in the description) anchoring element 3 (and all other anchoring elements) have an arch-like shape at their upper top part 5. Thus, as also shown in FIG. 3 an arched pointed edge on each anchoring element is provided which runs along the upper top part 5 of each anchoring element. As also explained in the context of FIG. 4 this arched pointed edge significantly improves the anchoring strength of the inventive suture in biological tissues.

Figure 4:
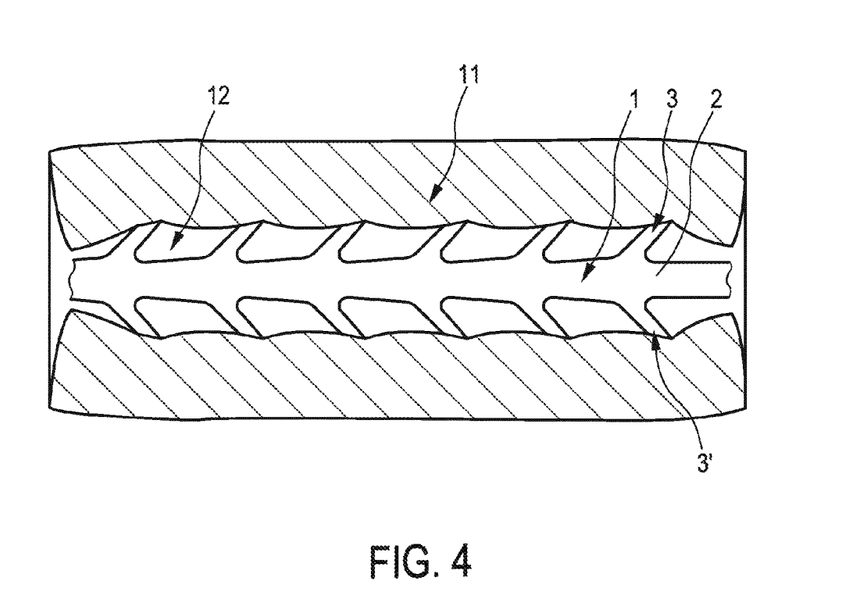
FIG. 4 is a schematic, cross-sectional view of an inventive surgical suture inserted and in contact with tissue.

FIG. 4 shows a situation in which surgical suture 1 according to the invention is inserted and anchored into tissue 11.

As shown and explained in FIGS. 1 and 2 the suture 1 with elongated body 2 and anchoring elements 3, 3' was inserted and pulled through tissue 11 into direction of the left side of FIG. 4 by means of a pointed end or surgical needle (not shown) attached to the left end of surgical suture 1. Due to the insertion and passage of suture 1 into tissue 11 a channel 12 was formed in the tissue.

Note that the passage of the suture 1 in the tissue 11 is hindered in the direction of the right site of FIG. 4, i.e. opposite direction where the anchoring elements point out, because the anchoring elements will stay in contact with the tissue surrounding suture 1 in channel 12.

In this context, FIG. 4 shows that the angular fin-like anchoring elements 3, 3' have a comparably great contact area between the upper top part of the anchoring element and the tissue. The pointed edge preferably provided in the front position during the anchoring process also contributes to the superior anchoring effect.

In contrast to this, in most existing commercial barbed sutures, the weak barb morphology provokes that the barb bends backwards under stress, thus reducing significantly its anchoring capacity.

Furthermore, mathematical simulation studies have demonstrated that above explained special feature of the inventive suture gives rise to an anchoring behavior which is independent of tissue stiffness. In this sense, the device does not need a critical tissue stiffness to work properly, having little sensitivity to this parameter. Simulation studies have also shown that this parameter is, however, vital in most of existing commercial barbed sutures that require of tissue stiffness to generate anchoring forces. Thus, whereas conventional barbed sutures require of a barb geometry optimization in order to achieve the optimal anchoring performance in a determined biological tissue, self-anchoring wound closure devices object of this invention will show an optimal anchoring behavior regardless of the characteristics of the biological tissue.

Figure 5:
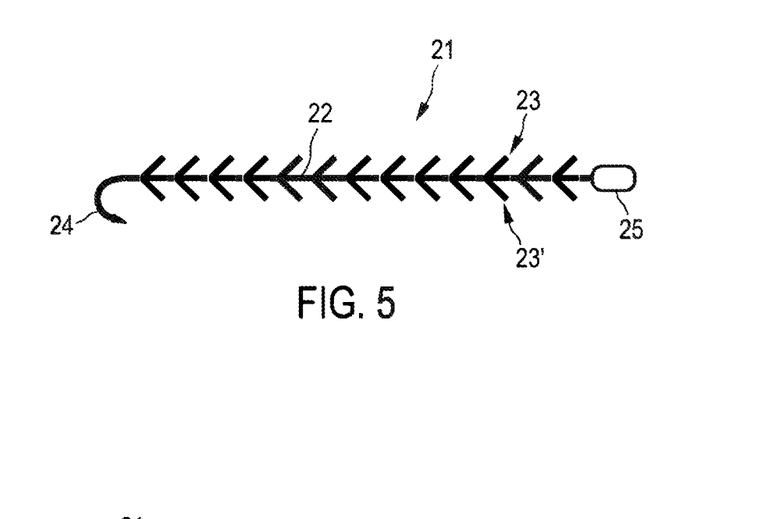
FIG. 5 is a schematic view of an inventive surgical suture with unidirectional configuration of its anchoring elements including a surgical needle and a stopping element.

Referring now to FIG. 5 this schematic drawing illustrates an inventive surgical suture with an unidirectional configuration of its anchoring elements including a surgical needle and a stopping element.

FIG. 5 illustrates in a schematic view an exemplary embodiment of an unidirectional surgical suture according to the present invention. This surgical suture 21 comprises an elongated body 22 wherein the inventive anchoring elements 23 and 23' with their fin-like design are only schematically illustrated. Anchoring elements 23 and 23' are disposed in two rows in which all anchoring elements 23, 23' have the same height H and the same distance G (not explicitly shown). All anchoring elements 23, 23' point to the same longitudinal direction. The inventive surgical suture 21 is provided with a surgical needle 24 (as an example for any other possible insertion device) at its proximal end and comprises a stopping element 25 having a flat tab-shape configuration at its distal end. The stopping element 25 can be formed by any suitable method known to those skilled in the art, however preferably according to the method illustrated in Example 2.

The flat tap-shaped stopping element 25 can have the dimensions as outlined earlier in the description. Preferably this stopping element in the form of a rectangular tab with rounded edges has a length (larger dimension) of 3.0 mm and a width of 1.5 mm. The thickness of the tab is preferably 0.15 mm.

Figure 6:
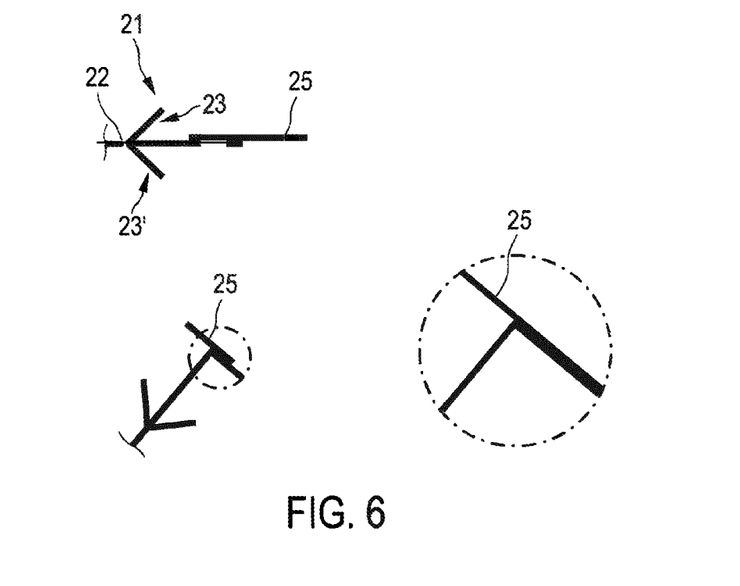
FIG. 6 is a schematic view of the functionality of the stopping element shown in FIG. 5.

In the context of the description of the surgical suture 21 in FIG. 5, FIG. 6 illustrates a preferred arrangement and function of stopping element 25 on surgical suture 21. According to FIG. 6 stopping element 25 can have two positions. At its initial position stopping element 25 (fixation tab) is arranged in a plane parallel to the elongated body 22 of surgical suture 21. When the surgical suture 21 passes through the tissue and the stopping element 25 comes in contact with the tissue, stopping element 25 is deployed in a plane perpendicular to the elongated body 22 of the surgical suture 21. This is a consequence of the resistance exerted against the tissue. Thus, as shown in FIG. 6 the second position of the stopping element 25 after deployment further fixes the position of the surgical suture 21 in the tissue after suture 21 has been anchored in the tissue via the anchoring elements 23, 23' provided on the elongated body 22 of the surgical suture 21.

Test results have shown that the holding strength of the stopping element 25 as illustrated in FIGS. 5 and 6 is at least equivalent or even statistically greater than the knot pull tensile strength requirement of synthetic absorbable monofilament (unbarbed) sutures of the same USP size designation.

Figure 7:
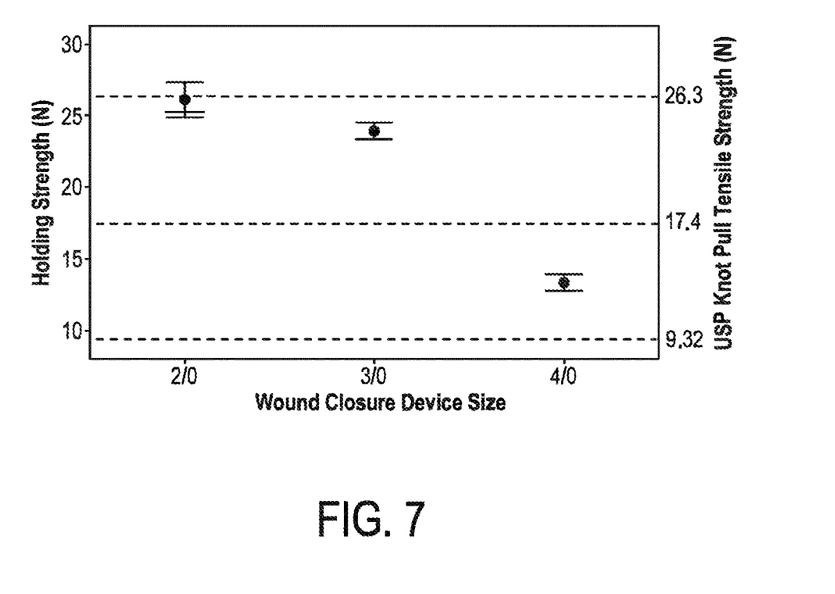
FIG. 7 shows measured holding strength values for an inventive surgical suture with a stopping element shown in FIGS. 5 and 6.

Referring in the latter context to FIG. 7, in this Figure the holding strength (in Newton N) of a stopping element 25 is shown for inventive wound closure devices of various sizes. For comparison, as dotted lines, the USP requirement for knot pull tensile strength (in Newton N) of a synthetic absorbable monofilament surgical suture (without any anchoring elements) is plotted also in FIG. 7. The corresponding values for a USP size of 2/0 is 26.3 N, for a USP size of 3/0 is 17.4 N, and for a USP size of 4/0 is 9.32 N.

As FIG. 7 clearly shows, the holding strength of the stopping element of all inventive wound closure devices with a corresponding size is at least as high as the USP knot pull tensile strength (e.g. size 2/0), or even considerably higher (e.g. for size 3/0 and size 4/0).

The invention claimed is:

1. A wound closure device comprising:
an elongated body having a longitudinal axis, a length and a cross-sectional area with a diameter; and
a plurality of projections protruding from said elongated body,
the plurality of projections comprising a first row of first anchoring elements arranged in a longitudinal direction of the elongated body and uniformly spaced along the length of the elongated body,
the plurality of projections further comprising a second row of second anchoring elements arranged in the longitudinal direction and uniformly spaced along the length of the elongated body,
each of the first anchoring elements and the second anchoring elements having a lower base part with a base length, an upper top part and a height,
each of the first anchoring elements in the first row being aligned diametrically with one of the second anchoring elements in the second row,
each of the first anchoring elements in the first row being separated from an adjacent one of said first anchoring elements in the first row by a section of the elongated body that extends an entire distance from a respective lower base part of each of the first anchoring elements to a respective lower base part of each adjacent one of the first anchoring elements, and
each section of the elongated body having an identically tapered shape in the longitudinal direction, wherein the identically tapered shape has a steady change in cross-sectional area, as viewed along the longitudinal axis of the elongated body, the identically tapered shape extending from the respective lower base part of each of the first anchoring elements to the respective lower base part of each adjacent one of the first anchoring elements.

2. The wound closure device according to claim 1, wherein the first row of first anchoring elements is offset from the second row of second anchoring elements at an angle of 180° relative to the longitudinal axis of the elongated body.

3. The wound closure device according to claim 1, wherein each of the first anchoring elements and the second anchoring elements has an arch shape.

4. The wound closure device according to claim 1, wherein the upper top part of each of the first anchoring elements and the second anchoring elements comprises at least one pointed edge.

5. The wound closure device according to claim 4, wherein the at least one pointed edge is defined by a point angle $\alpha \leq 70°$.

6. The wound closure device according to claim 4, wherein at least a majority of the pointed edges point in a same direction along the length of the elongated body.

7. The wound closure device according to claim 6, wherein all of the pointed edges point in said same direction along the length of the elongated body.

8. The wound closure device according to claim 1, further defining an inclination angle $\beta \leq 85°$ between the elongated body and each of the first anchoring elements and the second anchoring elements.

9. The wound closure device according to claim 1, wherein the height of at least the first anchoring elements is uniform.

10. The wound closure device according to claim 1, wherein a ratio between the diameter of the elongated body and the height of each of the first anchoring elements and the second anchoring elements is between 1:0.3 and 1:5.

11. The wound closure device according to claim 1, wherein at least a majority of the first anchoring elements have an identical orientation.

12. The wound closure device according to claim 1, wherein the elongated body comprises at least one portion without said plurality of projections.

13. The wound closure device according to claim 1, further comprising a pointed end at at least one end of the elongated body.

14. The wound closure device according to claim 1, further comprising at least one stopping element.

15. The wound closure device according to claim 1, further comprising a surgical needle at a first end of the elongated body and a stopping element at a second end of the elongated body, wherein the wound closure device is a surgical suture, and wherein all of the first anchoring elements and all of the second anchoring elements point in a same direction along the length of the elongated body.

16. The wound closure device according to claim 1, wherein the upper top part of each of the first anchoring elements and the second anchoring elements is arched.

17. The wound closure device according to claim 1, wherein a ratio between the diameter of the elongated body and a spacing between the first anchoring elements in the first row is between 1:0.8 and 1:15.

18. The wound closure device according to claim 1, wherein a ratio between the base length and a spacing between the first anchoring elements in the first row is between 1:0.8 and 1:6.

19. The wound closure device according to claim 1, wherein:

the lower base part of each of the first anchoring elements and the second anchoring elements extends along the base length from a front base end to a rear base end;

the upper top part of each of the first anchoring elements and the second anchoring elements extends from a front top end to a rear top end, wherein the upper top part tapers away from the longitudinal axis from the front top end to the rear top end;

each of the first anchoring elements and the second anchoring elements comprises a front edge joining the front base end to the front top end;

each of the first anchoring elements and the second anchoring elements comprises a rear edge joining the rear base end to the rear top end, wherein a portion of the rear edge joining the rear top end is parallel to the front edge; and the identically tapered shape in the longitudinal direction of each of the first anchoring elements and the second anchoring elements has a continuous taper away from the longitudinal axis from the respective rear base end each of the first anchoring elements and the second anchoring elements to the respective front base end of each adjacent one of the first anchoring elements and the second anchoring elements.

20. A method for producing a wound closure device according to claim 1 comprising the steps of:

pre-stretching the elongated body along its longitudinal direction;

creating cuts in the elongated body after pre-stretching; and stretching the elongated body along the longitudinal direction.

* * * * *